US005593639A

United States Patent [19]

Makino et al.

[11] Patent Number: 5,593,639

[45] Date of Patent: Jan. 14, 1997

[54] BLOOD-SAMPLING VESSEL

[75] Inventors: Kenya Makino; Yoshitaka Yamakawa, both of Tsuchiura; Mitsuhiro Murata, Tsukuba; Toshio Hayashi, Kyoto, all of Japan

[73] Assignee: Japan Synthetic Rubber Co., Ltd., Tokyo, Japan

[21] Appl. No.: 450,144

[22] Filed: May 26, 1995

[30] Foreign Application Priority Data

May 26, 1994 [JP] Japan .................................... 6-136548

[51] Int. Cl.[6] ................................ B01L 3/14; A61B 5/14

[52] U.S. Cl. ............................ 422/102; 422/99; 422/101; 128/760; 128/763; 128/766

[58] Field of Search ............................ 422/99, 101, 102; 424/78, 27; 526/240; 128/760–770

[56] References Cited

U.S. PATENT DOCUMENTS

| | | | |
|---|---|---|---|
| 3,901,219 | 8/1975 | Kay | 128/764 |
| 3,902,477 | 9/1975 | Gerarde | 128/760 |
| 4,112,925 | 9/1978 | Sullivan | 128/760 |
| 4,468,378 | 8/1984 | Voronkov et al. | 424/78.27 |
| 4,529,614 | 7/1985 | Burns | 427/2.11 |
| 4,639,339 | 1/1987 | Murashige et al. | |
| 4,991,601 | 2/1991 | Kasai et al. | 128/763 |
| 5,110,557 | 5/1992 | Brown et al. | 427/101 |
| 5,182,343 | 1/1993 | Ono et al. | 526/240 |

OTHER PUBLICATIONS

H. P. Gregor *Polym. Sci. Technol.* 1975, 7, 51–56.

H. P. Gregor *Chem. Abstr.* 1976, 84, 155623p.

L. C. Sedevel et al. *J. Biomed. Mater. Res.* 1981, 15, 819–827.

T. Barzu et al. *Biochem. J.* 1986, 238, 847–854.

J. Dawes *Anal. Biochem.* 1988, 174, 177–186.

K. Csomor et al. *Thromb. Res.* 1994, 74, 389–398.

Japanese No. 55075406, dated Jun. 6, 1980, English Abstract.

Japanese No. 61251770, dated Nov. 8, 1986, English Abstract.

Japanese No. 4210640, dated Jul. 31, 1992, English Abstract.

*Primary Examiner*—Arlen Soderquist

*Attorney, Agent, or Firm*—Oblon, Spivak, McClelland, Maier & Neustadt, P.C.

[57] ABSTRACT

A blood-sampling vessel containing therein a conjugated diene (co)polymer with a weight average molecular weight, reduced to sodium polystyrene sulfonate, of at least 3,000 and containing 2 mmol/g or more of at least one sulfonic acid group or a salt thereof. The vessel can be easily manufactured and constantly exhibits high anticoagulant and fibrinogen-removing capability to the blood contained therein, with no adverse effects on a variety of inspections and tests.

6 Claims, 5 Drawing Sheets

BLOOD-SAMPLING VESSEL

BACKGROUND OF THE INVENTION

1. Field of the Invention

The present invention relates to a vessel for sampling blood and, particularly, to a vessel for sampling blood which contains a conjugated diene (co)polymer comprising at least one group selected from a sulfonic acid group and a salt thereof which has anticoagulant or fibrinogen-removing capabilities.

2. Description of the Background Art

Along with the recent developments in clinical medicine, blood inspection technique used for diagnosis for preventing and treating diseases has become extremely important. Under this situation, various anticoagulants for preventing coagulation of blood samples collected for testing are being developed. Sodium heparin is known as an anticoagulant. An anticoagulant comprising a metal salt of ethylenediamine-tetraacetic acid is used for testing certain blood morphology. Because the anticoagulant comprising the sodium heparin can be obtained only by extraction from animal organs, not only is this anticoagulant difficult to produce in large amounts, but also the anticoagulant produced may be pathogenically contaminated. In addition, it is difficult to obtain heparin with the same structure and properties if different organs are used for the extraction.

Although the anticoagulant comprising a metal salt of ethylenediamine-tetraacetic acid can be used as an anticoagulant for testing blood morphology, the blood to which this anticoagulant has been added cannot be used for the quantitative analysis of inorganic ions, which is a type of biochemical test. This anticoagulant also hinders enzymatic testing of blood.

SUMMARY OF THE INVENTION

An object of the present invention is therefore to provide an easy-to-produce blood-sampling vessel containing an anticoagulant which constantly exhibits excellent anticoagulant and fibrinogen-removing capabilities and exhibits no adverse effects in performing various blood tests.

Another object of the present invention is to provide a blood-sampling vessel which enables to perform protein fractionation tests without problem and is capable of stably safely storing blood for a long period of time.

These objects have been achieved by the present invention by using an anticoagulant comprising a conjugated diene (co)polymer with a weight average molecular weight of at least 3,000 (the molecular weight reduced to sodium polystyrene sulfonate) which contains 2 mmol/g or more of at least one sulfonic acid group or a salt thereof (such a conjugated diene (co)polymer is hereinafter referred to as "specific conjugated diene (co)polymer").

Other objects, features and advantages of the invention will hereinafter become more readily apparent from the following description.

BRIEF DESCRIPTION OF THE INVENTION

DETAILED DESCRIPTION OF THE INVENTION AND PREFERRED EMBODIMENTS

Specific conjugated diene (co)polymer

Figure 1:
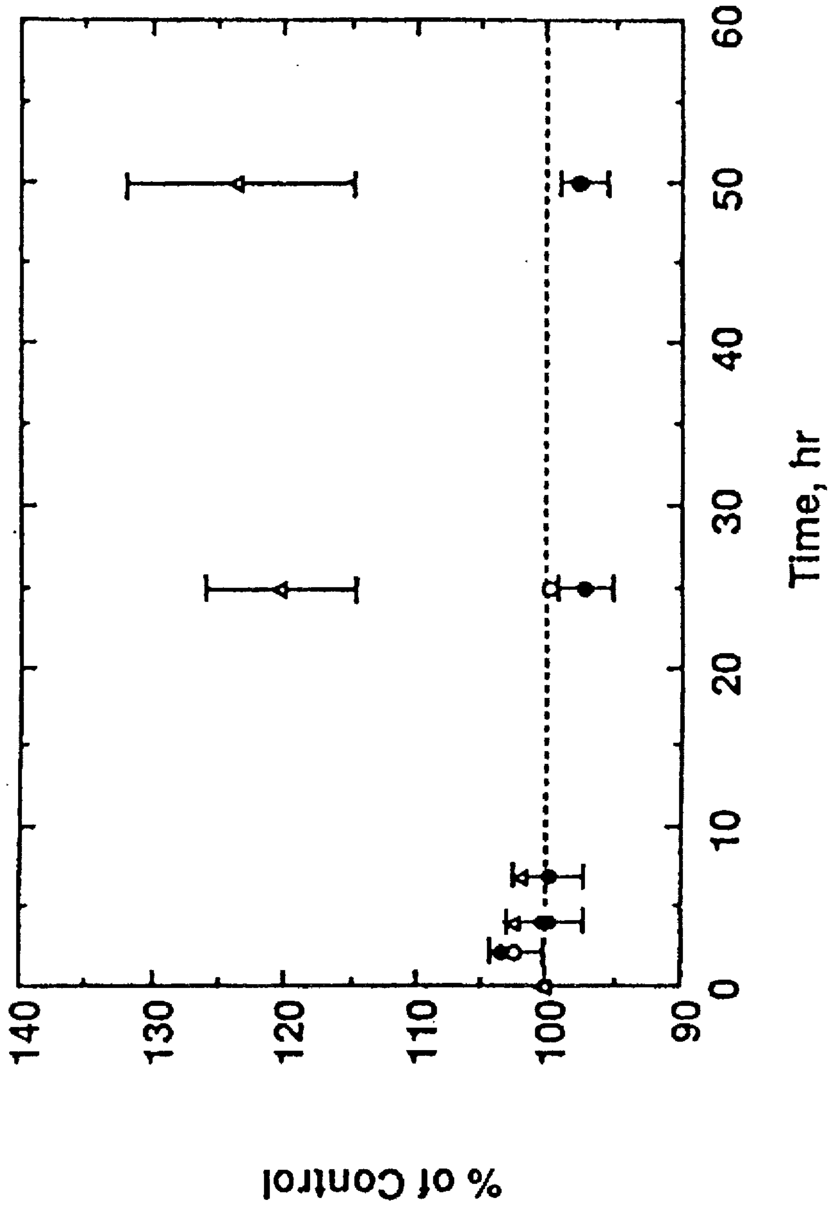
FIG. 1 shows the change of LDH over time in blood samples to which the specific sulfonated (co)polymer or heparin was added and in a control.

The specific conjugated diene (co)polymer used in the present invention may be either a block (co)polymer or a random (co)polymer. Further, it may be either (i) a conjugated diene polymer which is obtained by synthesizing a conjugated diene (co)polymer by the (co)polymerization of a conjugated diene and, optionally, other monomers copolymerizable with the conjugated diene (such a monomer is hereinafter referred to as "other monomer"), and then sulfonating this conjugated diene (co)polymer (hereinafter referred to as "sulfonated (co)polymer (I)"), or (ii) a conjugated diene polymer obtained by the (co)polymerization of a sulfonated conjugated diene and, optionally, other monomers (hereinafter referred to as "sulfonated (co)polymer (II)"). A part or all of the sulfonic acid group (—$SO_3H$) in the sulfonated (co)polymer (I) or (II) may be neutralized to a sulfonate group (—$SO_3X$, X: alkali metal, alkaline earth metal, or ammonium) by an alkali metal, an alkaline earth metal, or ammonia.

The weight average molecular weight (hereinafter referred to as "Mw") of the conjugated diene (co)polymer, reduced to the molecular weight of sodium polystyrene sulfonate, must be at least 3,000. It is preferably 4,000 to 500,000, and particularly preferably 5,000 to 500,000. If Mw is smaller than 3,000, the anticoagulant effect is insufficient. If Mw is extremely large, miscibility with blood is worsened, giving rise to insufficient removal of fibrinogen.

Furthermore, the total content of the sulfonic acid group or a salt thereof contained in the specific conjugated diene (co)polymer must be 2 mmol/g or more, preferably 4 mmol/g or more, and particularly preferably 4.2 to 7.5 mmol/g. The anticoagulant effect is-insufficient if this content is less than 2 mmol/g.

Process for the preparation of sulfonated (co)polymer (I)

The sulfonated (co)polymer (I) can be prepared according to the method described, for example, in Japanese Patent Laid-open (kokai) No. 227403/1990. An outline of this method is as follows.

(a) First, a conjugated diene (co)polymer is synthesized by (co)polymerizing a conjugated diene and, optionally, other monomers in the presence of a radical polymerization initiator, such as hydrogen peroxide, benzoyl peroxide, or azobisisobutyronitrile, or an anionic polymerization initiator, such as n-butyl lithium, sodium naphthalene, or metallic sodium, at −100° to 150° C., preferably at 0° to 130° C.

Linear or branched aliphatic dienes can be used as the conjugated diene. Examples are 1,3-butadiene, 1,3-pentadiene, 2,3-pentadiene, isoprene, 1,3-hexadiene, 1,4-hexadiene, 1,5-hexadiene, 2,3-hexadiene, 2,4-hexadiene, 2,3-dimethyl-1,3-butadiene, 2-ethyl-1,3-butadiene, 1,3-heptadiene, 1,4-heptadiene, 1,5-heptadiene, 2,5-heptadiene, 3,4-heptadiene, 3,5-heptadiene, 2-phenylbutadiene, and the like. These conjugated dienes can be used either alone or in combination of two or more.

Examples of the other monomer include aromatic compounds having a polymerizable double bond, such as styrene, α-methylstyrene, vinyltoluene, and p-methylstyrene; alkyl (meth)acrylate, such as methyl acrylate, ethyl acrylate, butyl acrylate, 2-ethylhexyl acrylate, methyl methacrylate, 2-hydroxyethyl acrylate, and 2-hydroxyethyl methacrylate; mono- or dicarboxylic acids having a polymerizable double bond, such as acrylic acid, methacrylic acid, crotonic acid, maleic acid, fumaric acid, and itaconic acid; acid anhydride of these dicarboxylic acid; cyanated compounds having a polymerizable double bond, such as acrylonitrile and methacrylonitrile; and other compounds having polymerizable double bond, such as vinyl chloride, vinylidene chloride, vinylmethyl ethyl ketone, vinyl methyl ether, vinyl acetate, vinyl formate, allyl acetate, methallyl acetate, acryl amide, methacryl amide, N-methylolacryl amide, glycidyl acrylate, glycidyl methacrylate, acrolain, allyl alcohol, and vinyl pyridine. Among these other monomers, aromatic compounds having polymerizable double bond, particularly styrene, are preferred. These other monomers can be used either alone or in combination of two or more.

The copolymerization proportion of these other monomers is-selected from a range such that the resulting (co)polymer contains the sulfonic acid group or a salt thereof in the amount defined in the present invention, and the preferable proportion is not more than 80 wt %, and a more preferable proportion is less than 50 wt %.

The conjugated diene (co)polymer in the present invention may be either blocked-type or random-type.

(b) The conjugated diene (co)polymer is then sulfonated.

The sulfonation is carried out on the double bonds in the conjugated diene (co)polymer using a sulfonation agent, such as sulfuric acid anhydride, fuming sulfuric acid, chlorosulfonic acid, or sodium hydrogen sulfite. Sulfuric acid anhydride alone or as a complex in combination with an electron donor compound is preferably used.

The electron donor compound used here may be selected from N,N-dimethylformamide; ethers, such as dioxane, dibutyl ether, tetrahydrofuran, and diethyl ether; amines, such as pyridine, piperazine, trimethylamine, triethylamine, and tributylamine; sulfides, such as dimethylsulfides and diethylsulfides; and nitriles, such as acetonitrile, ethylnitrile, and propylnitrile. Of these compounds, N,N-dimethylformamide and dioxane are preferred.

The sulfonation using the complex of sulfuric acid and the electron donor can be carried out by reacting the conjugated diene (co)polymer, as is or dissolved in a solvent which is inert to sulfuric acid anhydride, with the complex, while adding an appropriate amount of this complex which has been prepared in advance in a separate vessel. Chloroform, dichloromethane, dichloroethane, tetrachloroethane, nitromethane, nitrobenzene, propane, butane, pentane, hexane, cyclohexane, liquid sulfur dioxide, and the like are given as examples of the solvent inert to sulfuric acid anhydride. Two or more of these solvents can be used together as appropriate.

When sulfuric acid anhydride is used as the sulfonation agent, a sulfonate of the conjugated diene (co)polymer (hereinafter referred to as "intermediate"), in which the sulfuric acid anhydride is bonded to the conjugated diene (co)polymer, is obtained. In this instance, the intermediate is reacted with water or a basic compound, such as sodium hydroxide, potassium hydroxide, or ammonia. In this reaction, the double bond is cleaved by the bonding of the sulfonic acid or a salt thereof, or a hydrogen atom is substituted by the sulfonic acid or a salt thereof leaving the double bond as is. Thus, in this sulfonation reaction, the double bond is saturated into a single bond, or the sulfonic acid or a salt thereof is substituted for the hydrogen atom with no saturation of the double bond.

Process for preparing the sulfonated (co)polymer (II)

(a) In this process, first the sulfonation compound of a conjugated diene is prepared.

The conjugated dienes used here are linear or branched aliphatic dienes, such as 1,3-butadiene, 1,3-pentadiene, isoprene, 1,3-hexadiene, 2,4-hexadiene, 2,3-dimethyl-1,3-butadiene, 2-ethyl-1,3-butadiene, 1,3-heptadiene, 2,4-heptadiene, 3,5-heptadiene, 2-phenylbutadiene, and the like. These conjugated dienes can be used either alone or in combination of two or more.

The sulfonation of the conjugated diene can be carried out, for example, by adding the conjugated diene as is or dissolved in a suitable solvent, dropwise to a sulfonation agent in the manner described in Lecture on New Experimental Chemistry (Sin-Jikken Kagaku Koza), volume 14, Chapter 3, page 1773 (The Japanese Chemical Association).

In this instance, sulfuric acid anhydride may be used as the sulfonation agent alone or, more preferably, as a complex in combination with an electron donor compound.

The same electron donor compounds and solvents as mentioned in the illustration of the process for the preparation of sulfonated (co)polymer (I) can be used.

In this manner, a cyclic intermediate which is a sulfonate of the conjugated diene (generally called sultone) can be produced. This cyclic intermediated is reacted with a basic compound, such as sodium hydroxide, potassium hydroxide, or ammonia, to obtain a monomer with conjugated diene to which a sulfonic acid group is bonded. The sulfonation compound of the conjugated diene can be also obtained by adding water or alcohol to the cyclic intermediate to carry out dehydration or de-alcoholation.

(b) The sulfonated (co)polymer (II) can be prepared by (co)polymerizing the sulfonation compound of the conjugated diene, obtained in (a) above, and, optionally, other monomers copolymerizable with the sulfonation compound of the conjugated diene in the presence of a radical polymerizer or an anionic polymerizer at −100° to 150° C., preferably at 0° to 130° C. The sulfonation compound of the conjugated diene may be used either alone or in combination or two or more.

As the other monomer copolymerizable with the sulfonation compound of the conjugated diene, in addition to the same monomers mentioned in the illustration of the sulfonated (co)polymer (I), sulfonated compounds of these monomers, such as sulfonated styrene, can be given.

The copolymerization proportion of these other monomers is selected from a range such that the resulting (co)polymer contains the sulfonic acid group or a salt thereof in the amount defined in the present invention, and the preferable proportion is not more than 80 wt %, and a more preferable proportion is less than 50 wt %.

The sulfonated (co)polymer (I) and the sulfonated (co)polymer (II) may be used together in the blood-sampling vessel of the present invention.

Blood-sampling vessel

The blood-sampling vessel of the present invention contains the specific conjugated diene (co)polymer sealed therein. In this instance, the specific conjugated diene (co)polymer is used as a powder or a solution.

The powder of the specific conjugated diene (co)polymer can be obtained, usually, by removing water or the solvent in the reaction mixture after the synthesis, purifying it by removing low molecular weight components by dialysis, and lyophilizing the purified product.

The solution of the specific conjugated diene (co)polymer can be obtained by dissolving the purified powder of the specific conjugated diene (co)polymer in an aqueous medium which does not interfere with the testing of blood, preferably in a physiological salt solution. The concentration of the specific conjugated diene (co)polymer in the solution is usually about 0.01 to 10 wt %.

The term "blood-sampling vessel" as used in the present invention means a tubular receptacle or bottle for collecting and storing blood for testing, and includes tubes for systemic blood collection, serum separation, and glucose analysis. This tube is most appropriately applied as a vacuum blood-sampling tube. The vacuum blood-sampling tube is typically used as a system for collecting blood under vacuum and includes a holder and a suction needle for sampling blood.

Polyethylene terephthalate, polyacryl nitrile, polypropyrene, polyethylene, polystyrene, norbornene resins, glass, and the like are given as materials used for the blood-sampling vessel.

The volume of the blood-sampling vessel is usually 2 to 20 ml.

The amount of the specific conjugated diene (co)polymer sealed in the blood-sampling vessel in the present invention is 0.0001 to 2 mg, and preferably 0.01 to 1 mg, per 1 ml of blood to be collected. If this amount is less than 0.0001 mg, the anticoagulant and fibrinogen removing effects are not sufficient. An amount exceeding 2 mg may adversely affect testing of the blood.

The blood-sampling vessel of the present invention may contain, beside the specific conjugated diene (co)polymer, serum separator or small amounts of salt of heparin, oxalate, oxalic acid complex salt, citrate, and the like to the extent that there are no adverse effects on the blood tests.

If necessary, the blood-sampling vessel may be sterilized before or after the specific conjugated diene (co)polymer is sealed therein. The ethylene oxide gas method or the γ-ray method are given as the method of sterilization.

Other features of the invention will become apparent in the course of the following description of the exemplary embodiments which are given for illustration of the invention and are not intended to be limiting thereof.

EXAMPLES

The following methods were applied for the measurement of various properties and characteristics.

Measurement of sulfonic acid group and salts thereof

A 20 wt % solution of sulfonated (co)polymer (I) or (II) was prepared and purified by removing low molecular weight components using a dialyser (Spectrapore 6: trademark, manufactured by Spectrum Medical Industries Co., Mw cut-off 1000). A purified sample was converted into the complete acidic type by ion-exchange using an ion-exchange resin (Amberlight IR-118(H): trademark, manufactured by Japan Organo Co., Ltd.), to determine the amount of the sulfonic acid group by neutralization titration.

Mw

Mw was measure by gel permeation chromatography (GPC) using sodium polystyrene sulfonate as a standard sample.

Anticoagulant property 1.0 ml of fresh blood was taken in a sampler, homogenized several times, and allowed to stand. The occurrence or non-occurrence of blood coagulation was macroscopically observed at intervals of 30 minutes for 5 hours.

Amount of fibrinogen 0.9 ml of fresh blood was taken in a sampler and homogenized several times. 0.1 ml of thrombin (25 NIH unit/ml) was added to measure the time of coagulation at 37° C. The concentration of fibrinogen in the fresh blood was determined using a standard curve for the coagulation time and the concentration. This standard curve was prepared by diluting a purified fibrinogen solution of a known concentration to various concentrations and measuring the concentrations of these diluted solutions in the same manner.

Blood type determination 0.9 ml of fresh blood was taken in a sampler, homogenized, and centrifuged to separate the blood cells from the serum (or plasma). The blood cells were washed twice with a physiological salt solution and added to anti-A-type serum, anti-B-type serum, and anti-Rh-type serum. The serum (or plasma) were added to A-type erythrocyte and B-type erythrocyte. The degrees of erythrocyte coagulation in these samples were macroscopically observed to determine the blood types. The results were classified as follows:

++: Coagulated strongly

+: Coagulated

±: Difficult to judge

−: Not coagulated

Biochemical testing of blood 0.9 ml of fresh blood was taken in a sampler, homogenized, and centrifuged to separate the blood cells from the serum. Biochemical tests were carried out on the serum using the autoanalyzer Model 7250 (trademark, manufactured by Hitachi, Ltd.). The serum obtained from blood coagulated by allowing to stand without the addition of anticoagulants and by centrifuge was used as a control.

EXAMPLE 1

(1) 35.0 g of isoprene, 0.44 g of n-butyl lithium, and 200 g of cyclohexane were filled in a pressure vessel and polymerized for 4 hours while maintaining the temperature at 60° to 90° C. The polymerization was terminated by the addition of isopropyl alcohol (IPA).

After removing the solvent and unreacted monomers by evaporation under reduced pressure, the polymer was diluted with 1,2-dichloroethane to obtain a polymer solution.

(2) In a separate vessel, 32.9 g of sulfuric acid anhydride was added to 100 g of dioxane while maintaining the internal temperature at 25° C., followed by stirring for 2 hours to obtain a complex of sulfuric acid anhydride and dioxane.

(3) The complex of sulfuric acid anhydride and dioxane obtained in (2) was added to the polymer solution obtained in (1) in 2 hours while maintaining the internal temperature at 25° C. After the addition, the mixture was stirred for 2 hours, and 18.0 g of sodium hydroxide and 150 g of water were added. After stirring for a further 1 hour at 80° C., water and the solvent were removed by evaporation under reduced pressure. The resultant product was purified by dialysis and lyophilized to obtain a powdery sulfonated polymer (Ia). The total amount of sulfonic acid group and the salts thereof in this sulfonated polymer (Ia) and the results of Mw measurement are shown in Table 1.

(4) A 1% aqueous solution of the sulfonated polymer (Ia) thus obtained was prepared and 0.1 ml of the solution was sealed in a 2 ml vacuum blood sampling tube made of polyethylene.

(5) A sample of blood was taken using the vacuum blood sampling tube prepared in (4). The tests for anticoagulant properties, the amount of fibrinogen, blood-type determination, and biochemical blood tests were carried out on the sample. The results are shown in Tables 1–3.

EXAMPLES 2–7 AND COMPARATIVE EXAMPLES 1–2

(1) Powders of sulfonated polymer (I) containing the total amount of sulfonic acid group and the salts and Mw, shown in Table 1, were obtained in the same manner as in Example 1, provided that the monomer compositions shown in Table 1 were used, and the kind and quantity of the catalyst and the solvent in Example 1(1) and the kind of complex of sulfuric acid anhydride and dioxane in Example 1(2), and the amounts of the complex and sodium hyroxide in Example 1(3) were appropriately changed.

(2) A 1% aqueous solution of each of the sulfonated polymer (I) was prepared and 0.1 ml of the solution was sealed in a 2 ml vacuum blood sampling tube made of polyethylene.

(3) a sample of blood was taken using the vacuum blood sampling tube prepared in (2). The tests for anticoagulant properties, the amount of fibrinogen, blood-type determination, and biochemical blood tests were carried out on the sample. The results are shown in Tables 1 and 2.

EXAMPLE 8

(1) After replacing the atmosphere inside a pressure vessel with nitrogen, 400 ml of methylene chloride was filled in the vessel and 31 ml of dioxane was added. The mixture was allowed to cool to 5° to 10° C. while stirring. Then, 28.8 g of sulfuric acid anhydride was added dropwise to form a complex of sulfuric acid anhydride and dioxane, followed by a further reaction for 15 minutes.

150 ml of methylene chloride solution containing 24.5 g of isoprene was added dropwise over 1 hour to the resulting reaction solution. The mixture was stirred for 30 minutes after completion of the addition.

After the addition of 100 ml of aqueous solution of 14.4 g of sodium hydroxide, the mixture was evaporated under reduced pressure to remove the solvent and dioxane and dried to obtain 50.2 g of a product (crude sodium 2-methyl-1,3-butadiene-1-sulfonate).

This product was dissolved in 300 ml of water, 200 ml of toluene was added to the solution, and the mixture was vigorously shaken to extract toluene-soluble components from the water layer. The toluene layer was separated out and the water layer was dried to obtain sodium 2-methyl-1,4-butadiene-1-sulfonate (hereinafter referred to as "MBSN").

(2) 2 g of MBSN thus obtained was placed in a pressure bottle. After replacing the atmosphere inside the bottle with nitrogen, 15 ml of water and 0.06 g of sodium persulfate were added and the polymerization was carried out at 70° C. for 2 hours. The resultant product was purified by dialysis and lyophilized to obtain a sulfonated polymer (II). The total amount of sulfonic acid group and the salts thereof in this sulfonated polymer (II) and the results of Mw measurement are shown in Table 1.

(3) A 1% aqueous solution of the sulfonated polymer (II) thus obtained was prepared and 0.1 ml of the solution was sealed in a 2 ml vacuum blood sampling tube made of polyethylene.

(4) A sample of blood was taken using the vacuum blood sampling tube prepared in (3). The tests for anticoagulant properties, the amount of fibrinogen, blood-type determination, and biochemical blood tests were carried out on the sample. The results are shown in Tables 1–3.

EXAMPLES 9–10 AND COMPARATIVE EXAMPLES 3–4

(1) Powders of sulfonated (co)polymer (II) containing the total amount of sulfonic acid group and the salts and Mw, shown in Table 1, were obtained in the same manner as in Example 8(2), provided that the MBSN prepared in Example 8(1) and the monomers listed in Table 1 were used.

A 1% aqueous solution of each of the sulfonated (co)polymer (II) was prepared and 0.1 ml of the solution was sealed in a 2 ml vacuum blood sampling tube made of polyethylene.

A sample of blood was taken using the vacuum blood sampling tube. The tests for anticoagulant properties, the amount of fibrinogen, blood-type determination, and biochemical blood tests were carried out on the sample. The results are shown in Tables 1 and 2.

COMPARATIVE EXAMPLE 5

0.1 ml of a 0.01% aqueous solution of sodium heparin was sealed in a 2 ml vacuum blood sampling tube made of polyethylene.

A sample of blood was taken using the vacuum blood sampling tube. The tests for anticoagulant properties, the amount of fibrinogen, blood-type determination, and biochemical blood tests were carried out on the sample. The results are shown in Tables 1 and 2.

TABLE 1

| | Monomers (wt %) | Sulfonic acid group or the salts (mmol/g) | Mw | Coagulation of blood | Amount of fibrinogen (mg/dl) |
|---|---|---|---|---|---|
| Example 1 | Isoprene | 4.7 | 25600 | Not Coagulated | 0 |
| Example 2 | Isoprene | 5.1 | 30600 | Not Coagulated | 0 |
| Example 3 | Isoprene | 4.1 | 14400 | Not Coagulated | 0 |
| Example 4 | Isoprene | 5.0 | 19200 | Not Coagulated | 0 |
| Example 5 | 1,3-Butadiene | 4.8 | 24000 | Not Coagulated | 0 |
| Example 6 | 1,3-Pentadiene (88),styrene (12) | 4.7 | 15700 | Not Coagulated | 0 |
| Example 7 | Isoprene (68), styrene (32) | 5.1 | 21300 | Not Coagulated | 0 |
| Example 8 | MBSN | 5.5 | 20000 | Not Coagulated | 0 |
| Example 9 | MBSN(66), acrylic acid (34) | 4.5 | 26000 | Not Coagulated | 0 |
| Example 10 | MBSN(67), acrylamide (33) | 5.1 | 38000 | Not Coagulated | 0 |
| Example 11 | MBSN(42), sodium styrene sulfonate (58) | 5.3 | 5000 | Not Coagulated | 0 |
| Comparative Example 1 | Isoprene | 1.0 | 31000 | Coagulated | *1 |
| Comparative Example 2 | Isoprene | 4.2 | 2900 | Coagulated | *1 |
| Comparative Example 3 | MBSN | 1.2 | 33000 | Coagulated | *1 |
| Comparative Example 4 | MBSN | 5.8 | 170 | Coagulated | *1 |
| Comparative Example 5 | (Heparin) | — | — | Not Coagulated | 173 |

*1 Fibrin clots were produced, so the amount of fibrinogen could not be measured.

TABLE 2

| | Degree of Blood Coagulation | | | | | |
|---|---|---|---|---|---|---|
| | Anti-A-type serum | Anti-B-type serum | A-type erythrocyte | B-type erythrocyte | Anti-Rh-type serum | Blood-type |
| Example 1 | − | − | ++ | + | ++ | O-type Rh+ |
| Example 2 | − | − | ++ | + | ++ | O-type Rh+ |
| Example 3 | − | − | ++ | + | ++ | O-type Rh+ |
| Example 4 | − | − | ++ | + | ++ | O-type Rh+ |
| Example 5 | − | − | ++ | + | ++ | O-type Rh+ |
| Example 6 | − | − | ++ | + | ++ | O-type Rh+ |
| Example 7 | − | − | ++ | + | ++ | O-type Rh+ |
| Example 8 | − | − | ++ | + | ++ | O-type Rh+ |
| Example 9 | − | − | ++ | + | ++ | O-type Rh+ |
| Example 10 | − | − | ++ | + | ++ | O-type Rh+ |
| Example 11 | − | − | ++ | + | ++ | O-type Rh+ |
| Comparative Example 1 | − | − | + | ± | + | O-type Rh+ |
| Comparative Example 2 | − | − | + | ± | + | O-type Rh+ |
| Comparative Example 3 | − | − | + | ± | + | O-type Rh+ |
| Comparative Example 4 | − | − | + | ± | + | O-type Rh+ |
| Comparative Example 5 | − | − | ++ | + | + | O-type Rh+ |

TABLE 3

| | Unit | Example 1 | Example 8 | Control |
|---|---|---|---|---|
| TP (Total protein) | g/dl | 7.0 | 6.9 | 7.1 |
| AST (Aspartate aminotransferase) | U | 16.2 | 17.5 | 22.8 |
| ALT (Alanine aminotransferase) | U | 21.1 | 21.1 | 21.0 |
| LDH (Lactate dehydrogenase) | ×10 U/l | 225 | 217 | 246 |
| AMY (Amylase) | ×10 U/l | 52.6 | 50.3 | 65.9 |
| CPK (Creatine kinase) | mg/dl | 109 | 107 | 132 |
| BUN (Blood urea nitrogen) | mg/dl | 12.8 | 12.5 | 13.4 |
| CHE (Cholinesterase) | mg/dl | 0.8 | 0.8 | 1.0 |
| Na | mg/dl | 146 | 148 | 142 |
| K | mg/dl | 3.8 | 4.0 | 4.0 |
| Cl | mg/dl | 108 | 110 | 106 |
| Ca | mg/dl | 8.9 | 8.9 | 9.8 |

TEST EXAMPLE 1

1 ml of fresh blood was added to blood sampling tubes prepared in Example 1 and Comparative Example 5, homogenized several times, and stored at 4° C. for 2 days. Coagulation of the blood was judged by macroscopic observation. It was found that there was no change in the blood in the sampling tube prepared in Example 1, while the blood in the sampling tube of Comparative Example 5 coagulated.

Figure 2:
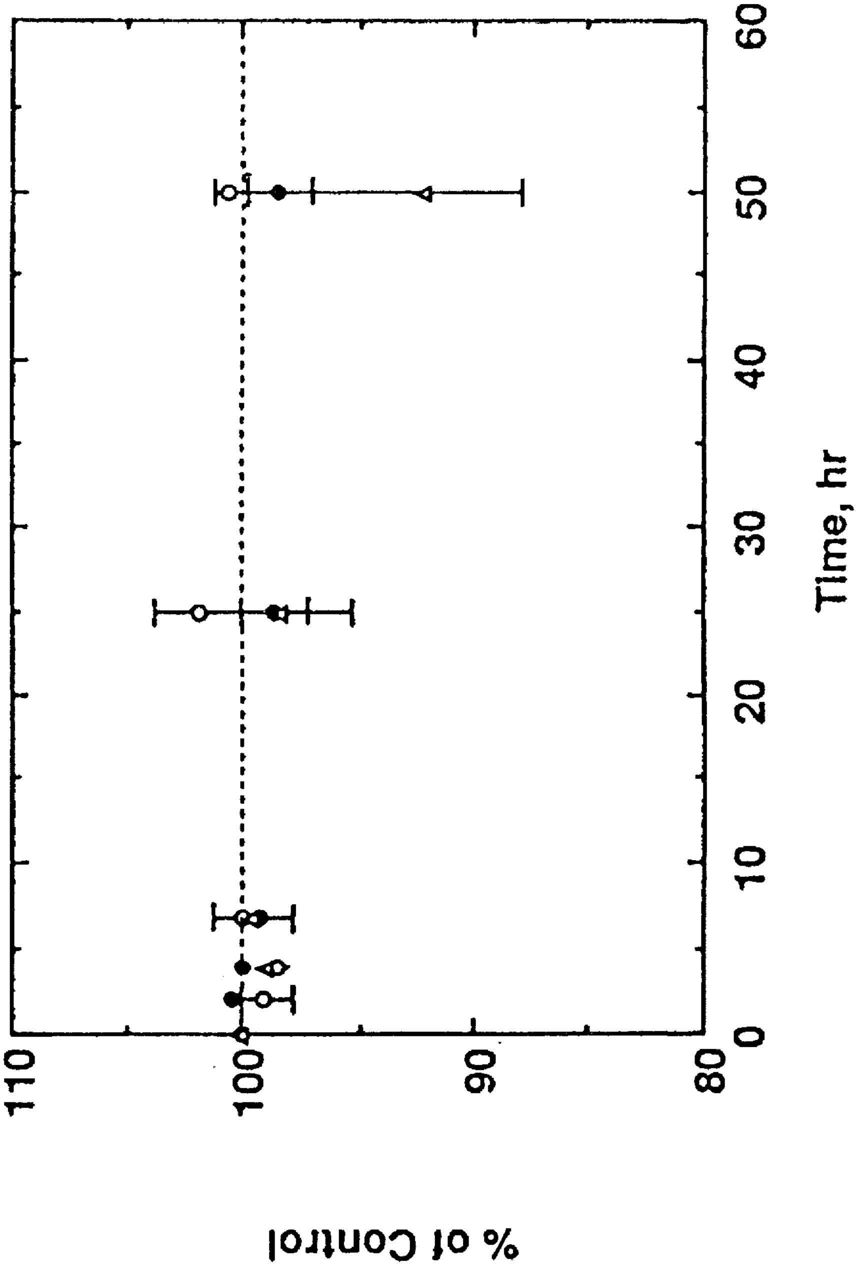
FIG. 2 is chart similar to FIG. 1, showing the change of GLU over time in blood samples.

Changes over time of LDH and GLU (glucronic acid) were measured on blood samples to which the specific sulfonated (co)polymer JAC (Mw: 30,000, sulfonation: 4.6 mmol/g, concentration: 0.3 mg/ml) or heparin was added and on a control from which serum was removed by spontaneous coagulation. The results are shown in FIGS. 1 and 2, wherein solid circles indicate the results of the blood sample to which the specific sulfonated (co)polymer was added; open triangles, that to which heparin was added; and open circles, the control.

TEST EXAMPLE 2

Figure 3:
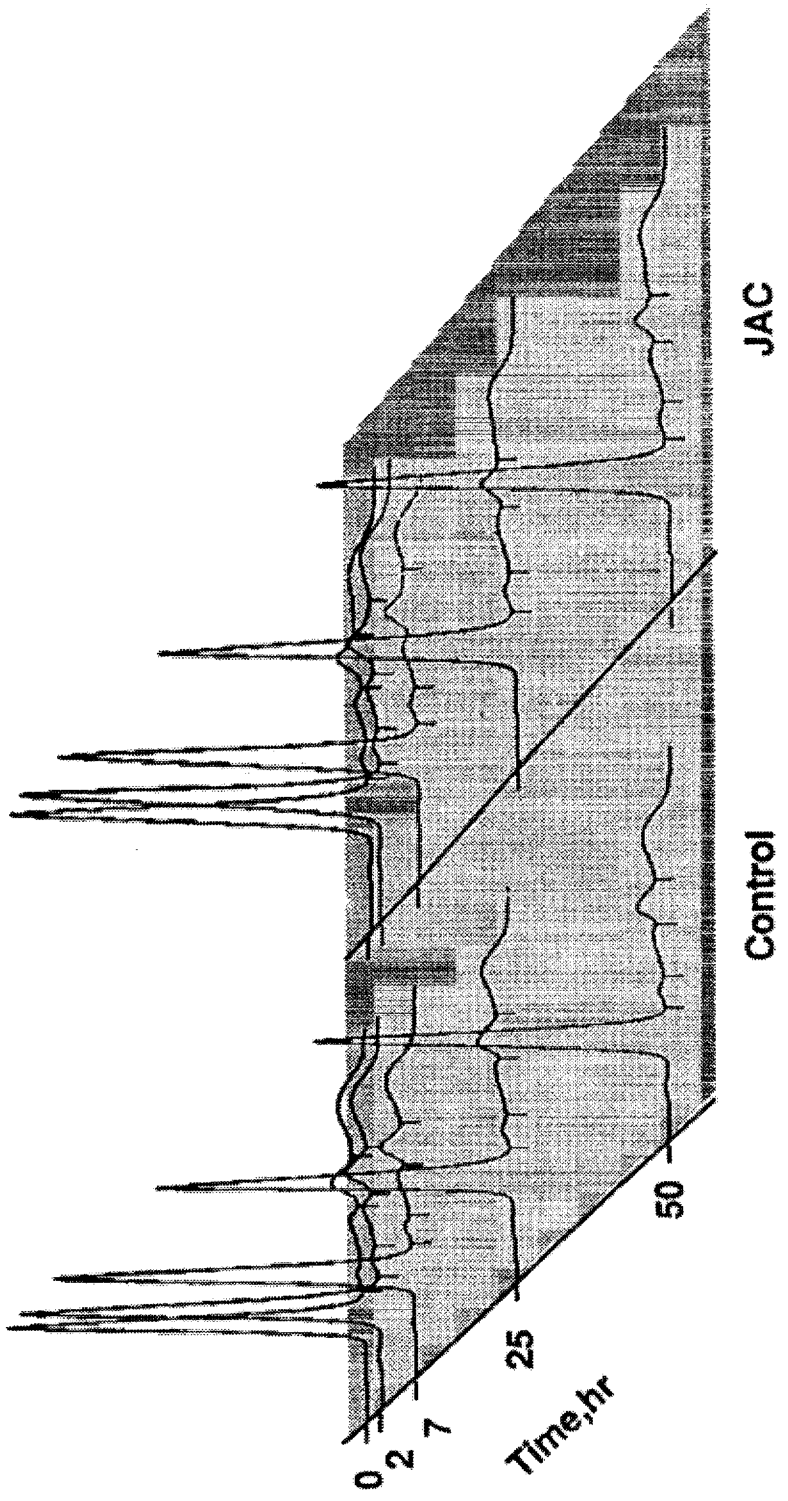
FIG. 3 shows profiles of electrophoresis over time for a blood sample to which the specific sulfonated (co)polymer was added and for a control.

Changes in protein fractions over time were measured by electrophoresis on a blood sample to which sulfonated polyisoprene JAC (Mw: 30,000, sulfonation: 4.6 mmol/g, concentration: 0.3 mg/ml) was added and on a control from which fibrinogen was removed by spontaneous coagulation. The results are shown in FIG. 3.

TEST EXAMPLE 3

Figure 4:
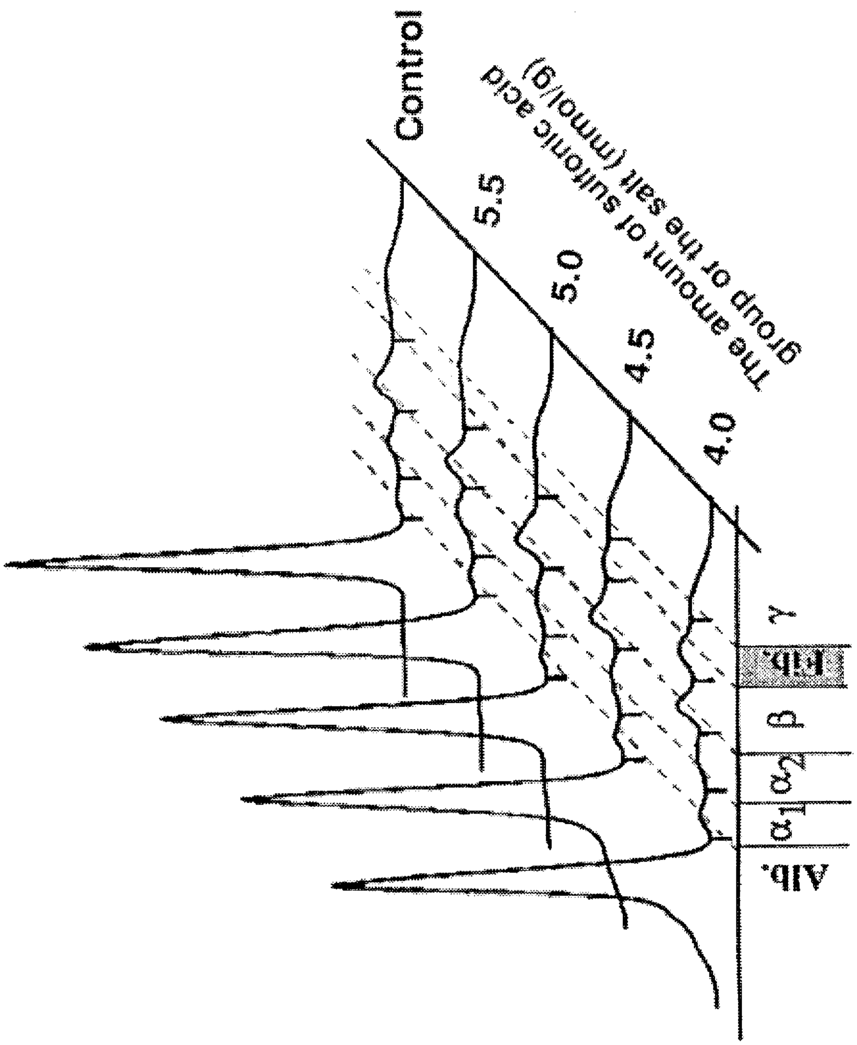
FIG. 4 shows profiles of electrophoresis of blood samples to which the specific sulfonated (co)polymers with different amounts of sulfonic acid group or a salt thereof were added, and, of a control.

Protein fractions were measured by electrophoresis of blood samples to which sulfonated polyisoprene with a different total amount of sulfonic acid group or a salt thereof were added and on a control from which fibrinogen was removed by spontaneous coagulation. The results are shown in FIG. 4, wherein Alb. stands for albumin; $\alpha_1$, $\alpha_1$-globulin; $\alpha_2$, $\alpha_2$-globulin; $\beta$, $\beta$-globulin; $\gamma$, $\gamma$-globulin; and Fib., fibrinogen.

TEST EXAMPLE 4

Protein fractions were measured by electrophoresis of the following blood samples:

JAC: A blood sample to which 0.3 mg of sulfonated polyisoprene per 1 ml of blood was added.

JAC+Heparin: A blood sample to which 0.3 mg of sulfonated polyisoprene and 0.03 mg of sodium heparin per 1 ml of blood were added.

Heparin: A blood sample to which sodium heparin was added.

Control: A blood sample from which fibrinogen was removed by spontaneous coagulation.

Figure 5:
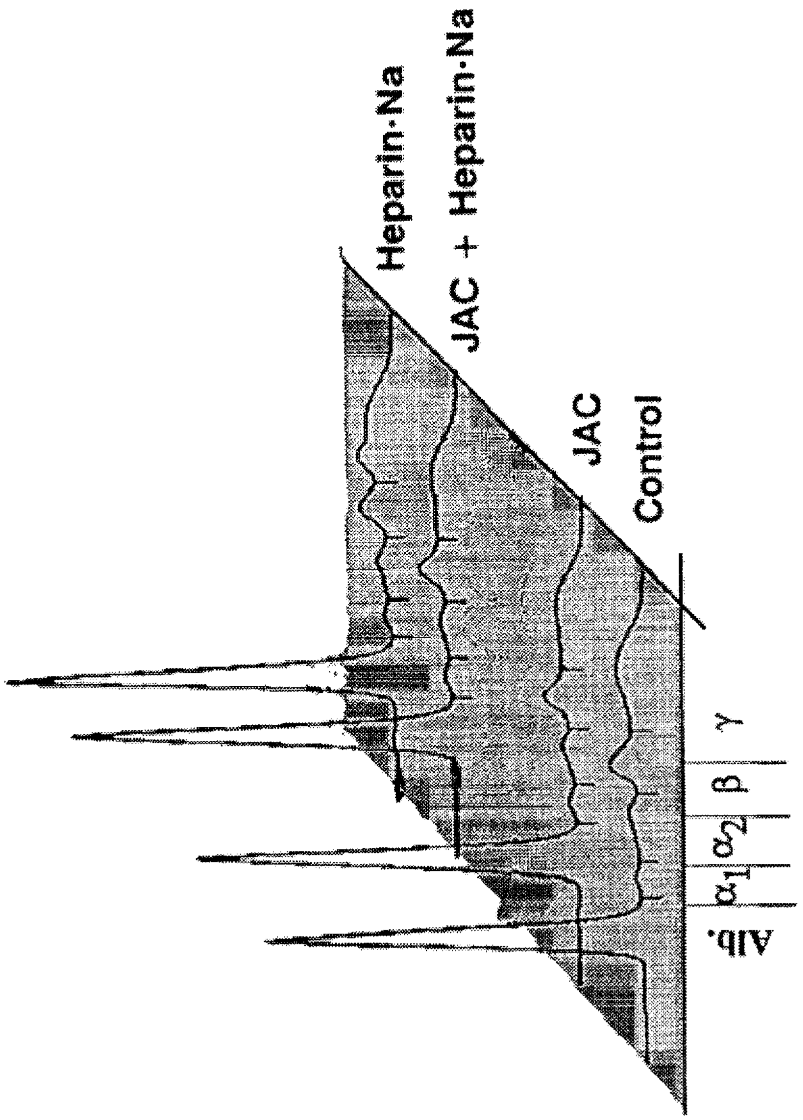
FIG. 5 shows profiles of electrophoresis of blood samples to which different anticoagulants were added.

The results are shown in FIG. 5, wherein the various abbreviations have the same meanings as in FIG. 4.

The vessel for sampling blood of the present invention can be easily manufactured and constantly exhibits high anticoagulant and fibrinogen-removing capabilities to the blood contained therein. The vessel has no adverse effects on a variety of tests and inspections, including the protein fractionation test. Because there is no half life for the anticoagulant used in the vessel of the present invention as in the case of heparin sodium, it can stably store blood for a long period of time.

What is claimed is:

1. A vessel comprising a blood-sampling vessel containing therein an anticoagulating comprising an conjugated diene polymer with a weight average molecular weight, reduced to sodium polystyrene sulfonate, of at least 3,000 and containing 2 mmol/g or more of at least one sulfonic acid group or a salt thereof.

2. The vessel according to claim 1, wherein said conjugated diene polymer contains 4 mmol/g or more of at least one sulfonic acid group or a salt thereof.

3. The vessel according to claim 1, wherein said conjugated diene polymer has a weight average molecular weight, reduced to sodium polystyrene sulfonate, of 5,000 to 500,000.

4. The vessel according to claim 1, wherein said conjugated diene polymer is a polymer of isoprene or polyisoprene.

5. The vessel according to claim 1, containing 0.0001 to 2 mg of said conjugated diene polymer per 1 ml of blood.

6. The vessel according to claim 1, wherein said blood-sampling vessel is a vacuum blood-sampling vessel.

* * * * *